United States Patent
Morita et al.

(10) Patent No.: US 6,797,237 B2
(45) Date of Patent: Sep. 28, 2004

(54) OXIDATION DECOMPOSITION TYPE ELEMENT ANALYZER

(75) Inventors: Yozo Morita, Kameoka (JP); Takeshi Iharada, Nagaokakyo (JP)

(73) Assignee: Shimadzu Corporation, Kyoto (JP)

(*) Notice: Subject to any disclaimer, the term of this patent is extended or adjusted under 35 U.S.C. 154(b) by 221 days.

(21) Appl. No.: 10/015,678

(22) Filed: Dec. 17, 2001

(65) Prior Publication Data

US 2003/0044998 A1 Mar. 6, 2003

(30) Foreign Application Priority Data

Aug. 31, 2001 (JP) ........................................ 2001-263614

(51) Int. Cl.[7] ........................ G01N 31/12; G01N 21/29; G01N 21/41; G01N 21/00; G01N 15/06
(52) U.S. Cl. ........................ 422/78; 422/50; 422/68.1; 422/80; 422/82.05; 422/83; 436/43; 436/103; 436/106; 73/1.01; 73/1.02; 73/23.2
(58) Field of Search ........................ 422/50, 68.1, 80, 422/82.05, 83, 78; 436/43, 103, 106; 73/1.01, 1.02, 23.2

(56) References Cited

U.S. PATENT DOCUMENTS

| | | | |
|---|---|---|---|
| 4,277,438 A | * | 7/1981 | Ejzak .......................... 422/80 |
| 5,132,094 A | * | 7/1992 | Godec et al. ............... 422/68.1 |
| 5,531,961 A | * | 7/1996 | Wright et al. ................ 422/80 |
| 6,375,900 B1 | * | 4/2002 | Lee-Alvarez et al. ......... 422/80 |

* cited by examiner

Primary Examiner—Jill Warden
Assistant Examiner—Brian Sines
(74) Attorney, Agent, or Firm—Manabu Kanesaka

(57) ABSTRACT

In an analyzer, an oxidation reagent is supplied to an oxidation reaction portion, and after organic materials contained in the oxidation reagent are removed by oxidation decomposition, a sample is provided into the oxidation reaction portion to react with the oxidation reagent. An infrared gas analyzing portion starts detecting a peak for analyzing. Thus, even if a concentration of the component to be measured in the sample is low, the concentration can be measured accurately without being disturbed by a concentration of the impurities in the oxidation reagent.

4 Claims, 3 Drawing Sheets

OXIDATION DECOMPOSITION TYPE ELEMENT ANALYZER

BACKGROUND OF THE INVENTION AND RELATED ART STATEMENT

The invention relate to an analyzer for measuring impurities, such as an organic material, nitrogen compound and phosphorus compound contained in water, in particular, an analyzer adapting a wet oxidation decomposition system.

As a subject to be analyzed, there is mentioned extra-pure water widely used in the semiconductor manufacturing industry and pharmaceutical manufacturing industry, or for cooling in the nuclear power generation plant.

In the wet oxidation decomposition type analyzer, an oxidizing reagent together with a sample is added to an oxidation reactor in the oxidation decomposition process. Generally, since impurities are also contained in the oxidizing reagent, a sum of a measured value, i.e. true value, of a sample component to be measured and a background due to the impurities contained in the oxidizing reagent can be obtained as a measured value. Since these values can not be separated, it is necessary that the measured value, i.e. background, of only the oxidizing reagent without adding the sample thereto is separately measured, and the value is subtracted from the above-mentioned measured value to thereby obtain the measured value, i.e. true value, of the sample to be measured.

Since the result can be obtained by subtracting the measured value of only the oxidizing reagent from the sum of the measured value of the sample component to be measured and the background of the oxidizing reagent, in case the measured value, i.e. true value, of the sample component is sufficiently high when compared with the background of the oxidizing reagent, there is no problem. However, as in a case of measuring an extra-pure water, when the measured value or true value of the sample is especially lower than the background of the oxidizing reagent, there is a problem such that the accuracy of the measured result is extremely decreased.

In view of the above problems, the present invention has been made and an object of the invention is to provide a wet oxidation decomposition type element analyzer, wherein even if a concentration of a subject to be measured in a sample is low, it is possible to measure the concentration accurately without being disturbed by the concentration of the impurities of the oxidizing reagent.

Further objects and advantages of the invention will be apparent from the following description of the invention.

SUMMARY OF THE INVENTION

In the present invention, an oxidation decomposition process for oxidizing only an oxidizing reagent in an oxidization reaction portion is provided right before a sample measurement. More specifically, an analyzer according to the present invention is a wet oxidation decomposition type analyzer, wherein the oxidizing reagent together with the sample is added to the oxidation reaction portion, and the oxidized component to be measured is measured at the analyzing portion to thereby obtain a concentration of the component to be measured. The analyzer includes a controlling portion for controlling operations for supplying the sample and the oxidizing reagent to the oxidization reaction portion, respectively. The controlling portion controls supplies of the sample and oxidizing reagent such that the oxidizing reagent is supplied to the oxidization reaction portion before the sample is supplied thereto, and then the sample is supplied thereto after elapse of a time during which the impurities contained in the oxidizing reagent are removed by the oxidization decomposition at the oxidization reaction portion.

First, the impurities contained in only the oxidizing reagent are removed through the oxidation decomposition at the oxidation reaction portion, and then, the sample is added thereto so that the sample is subjected to the oxidation decomposition with the oxidizing reagent from which the impurities have already been removed. Since the measured value obtained by the oxidization decomposition of the sample does not contain the background of the impurities contained in the oxidizing reagent, the true value of the sample component can be obtained.

DETAILED DESCRIPTION OF THE PREFERRED EMBODIMENT

Figure 1:
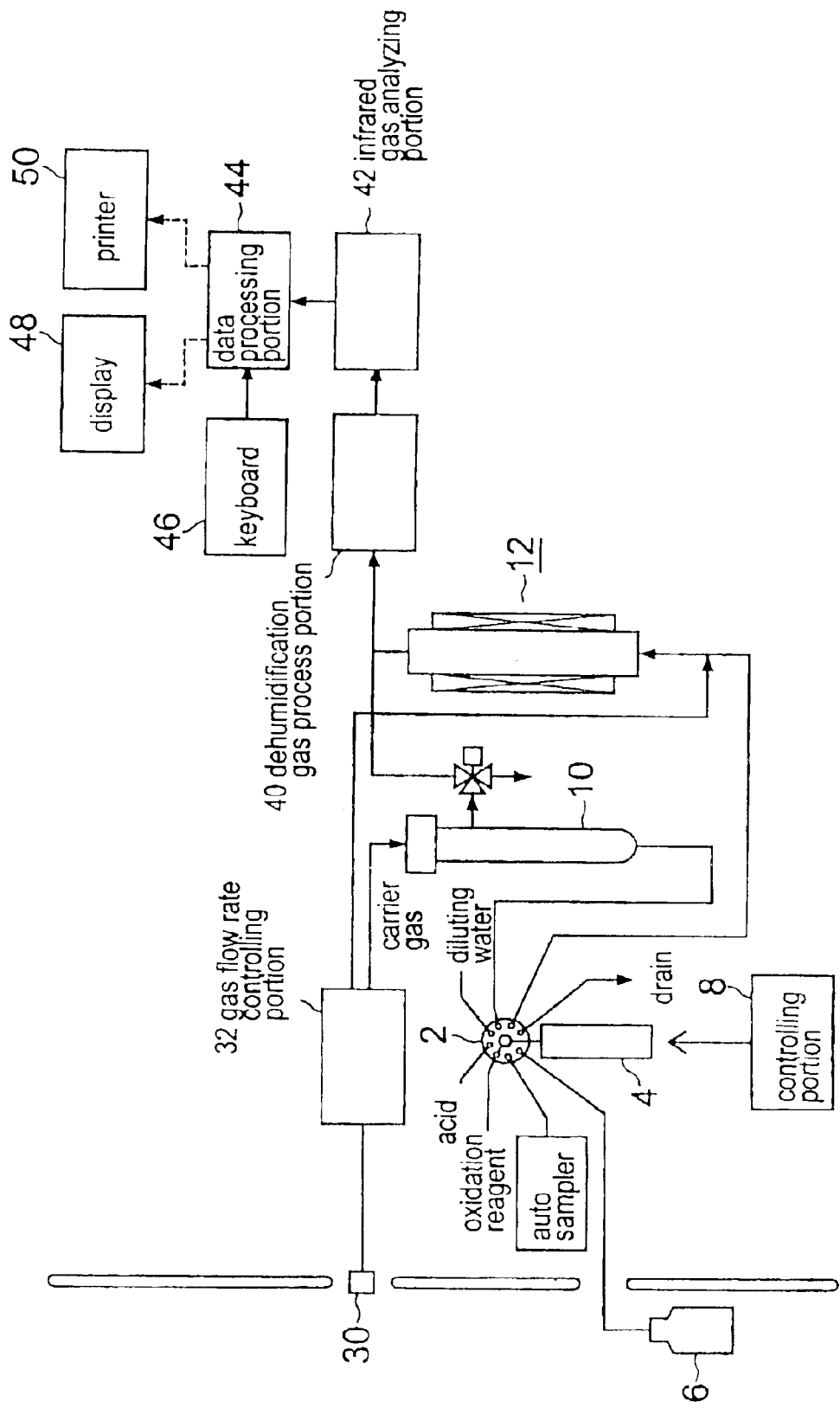
FIG. 1 is a block diagram showing a structure of an embodiment according to the present invention.

With reference to a measurement system diagram as shown in FIG. 1, an embodiment of the invention will be explained hereunder. This is an apparatus for measuring a total organic carbon (hereinafter referred to as "TOC") in water.

An automatic sample injection system includes an eight port rotary valve 2, and a syringe 4 connected to a common port thereof, both of which are driven by a motor.

The respective ports of the eight port rotary valve 2 are connected to a passage connected to outer sample water 6; a passage connected to an auto-sampler for supplying a sample; a passage for supplying an oxidizing agent to be used in an oxidation reaction portion 12; a passage for supplying acid for acidifying the sample water in inorganic carbon (hereinafter referred to IC) sparger 10; a passage for supplying a dilution water for diluting the sample; a passage connected to the IC sparger 10; a passage connected to the oxidation reaction portion 12; and a passage connected to a drain outlet for discharging a measured or unnecessary liquid, respectively.

Reference numeral 8 represents a control portion for controlling operations of the valve 2 and the syringe 4, which forms a characteristic part of the present invention.

When acid is supplied to the IC sparger 10 together with the sample and then carrier gas is blown thereinto, an inorganic carbon compound in the sample is expelled to a detection portion as carbon dioxide to thereby measure an inorganic carbon concentration.

Figure 2:
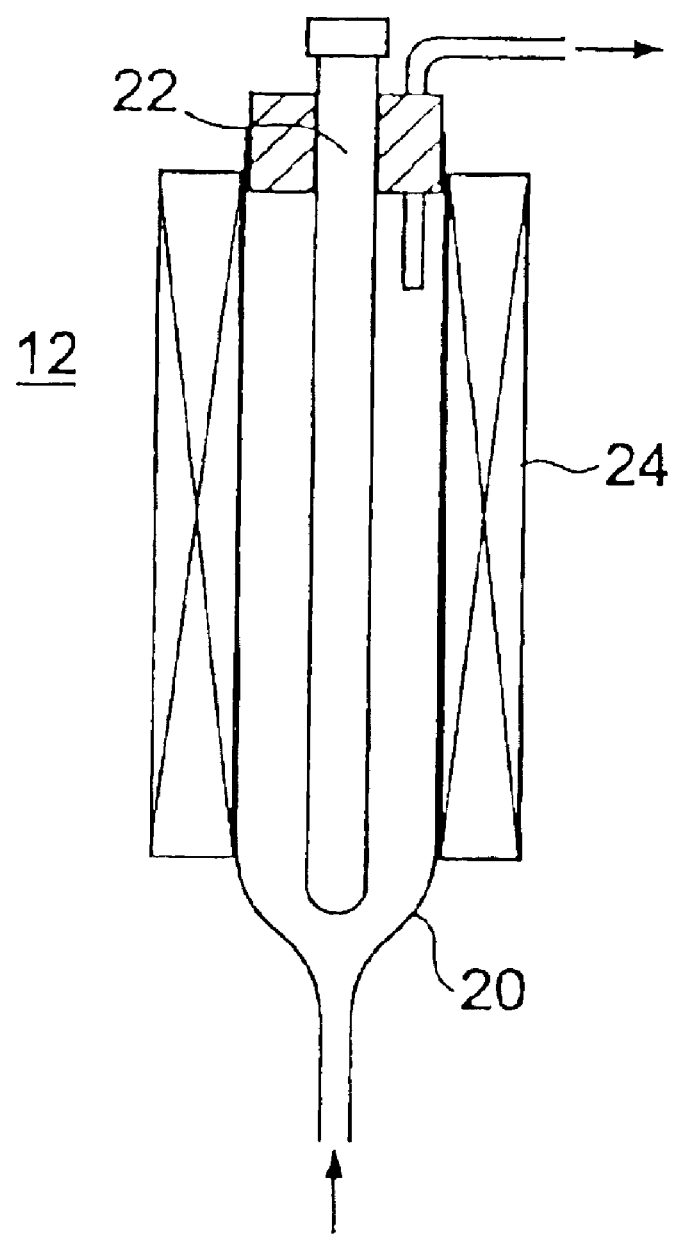
FIG. 2 is a sectional view showing an oxidization reaction portion of the embodiment.

As an inner structure of the oxidation reaction portion 12 is shown in FIG. 2, an ultraviolet (hereinafter referred to as "UV") lamp 22 is disposed at the center portion of a glass container 20, and the sample, oxidizing agent and carrier gas are supplied from a bottom portion of the glass container 20. The glass container 20 is surrounded by a heater 24 to thereby keep a temperature therein at a predetermined value. Carbon dioxide generated through the oxidation decomposition is introduced into an analyzing portion together with the carrier gas from an upper portion of the glass container 20.

The carrier gas is supplied to the IC sparger 10 and the oxidation reaction portion 12, respectively, from a carrier gas supply port 30 through a gas flow rate controlling portion 32.

The gases generated at the IC sparger 10 and the oxidation reaction portion 12 together with the carrier gas are introduced into an infrared gas analyzing portion 42 formed of a non-dispersion type infrared light meter (hereinafter referred to as "NDIR") for detecting carbon dioxide through a dehumidification gas process portion 40 provided with an electronic cooler for removing a water content and a halogen scrubber for removing a halogen component. An output of the analyzing portion 42 is inputted into a data process portion 44. The data process portion 44 is connected to a key board 46, a display 48 and a printer 50.

Through an automatic sample injection system formed of the eight port rotary valve 2 and the syringe 4, the sample can be taken and measured, and then injected into the IC sparger 10 and the oxidation reaction portion 12, or discharged therefrom. In addition to this, predetermined amounts of the oxidizing agent and acid can be injected into or discharged from the oxidation reaction portion 12 and IC sparger 10, or the sample can be diluted by diluting water.

Since the oxidation reaction portion 12 is provided therein with an ultraviolet lamp, organic materials contained in the sample injected thereto are totally oxidized by the actions of the oxidizing agent and ultraviolet rays and converted into carbon dioxide. The thus generated carbon dioxide is brought into an infrared gas analyzing portion 42 by the carrier gas flowing through the oxidation reaction portion 12 to measure a concentration thereof. Since the non-dispersion type infrared light meter is used as the infrared gas analyzing portion 42 and the carbon dioxide is measured by a flow cell, the signal becomes a peak shape and its area is in proportion to the concentration.

The device is corrected by measuring a standard sample containing already known organic materials, and an unknown sample is measured by the device based on the corrected results.

Figure 3:
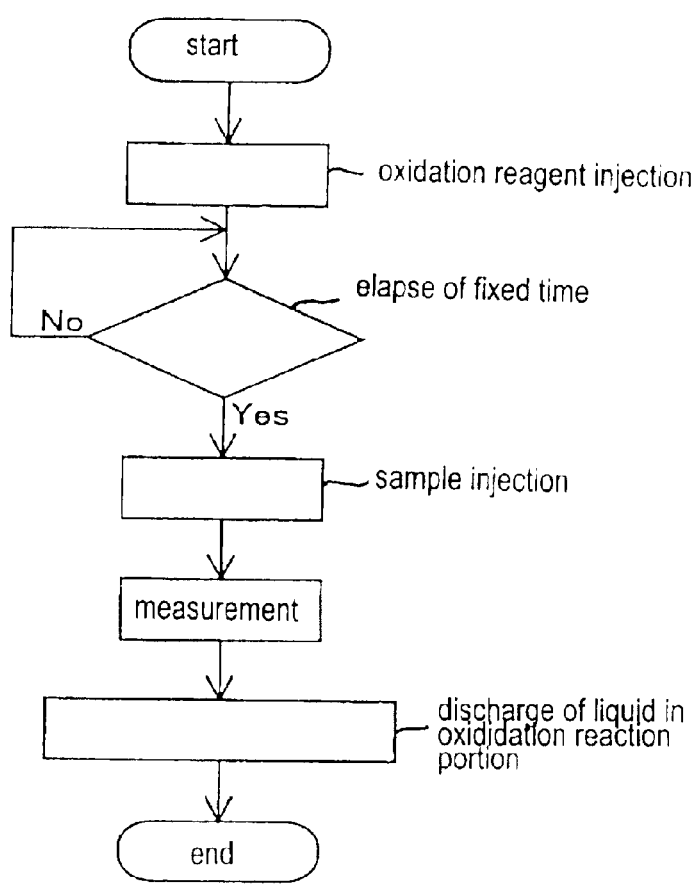
FIG. 3 is a flow chart mainly showing an operation of a controlling portion in the embodiment.

In the present embodiment, operations carried out mainly by the controlling portion 8 are sequentially explained with reference to FIG. 3.

(1) A predetermined amount, for example 1.5 ml, of the oxidizing reagent is injected into the oxidation reaction portion 12. The oxidizing reagent is excessively injected so that the subject to be analyzed in the sample is totally oxidized.

(2) Watch and wait for, for example, 90 seconds. During the period, the organic materials contained in the oxidizing reagent are subjected to the oxidation decomposition to be removed. Although a peak of the background appears in the infrared gas analyzing portion 42, this is neither measured nor displayed on a screen of the analyzer.

(3) A predetermined amount, for example 3 ml, of the sample is injected into the oxidation reaction portion 12, and at the same time, detection of the peak starts at the infrared gas analyzing portion 42 to display the measured peak on the screen.

(4) After termination of the peak, the oxidized sample in the oxidation reaction portion 12 is returned to the syringe 4 together with the oxidizing reagent and discharged to the drain thus completing the measurement.

The measured peak is subjected to an area calculation and compared with the corrected result which has been obtained beforehand to thereby calculate a concentration thereof.

Figure 4:
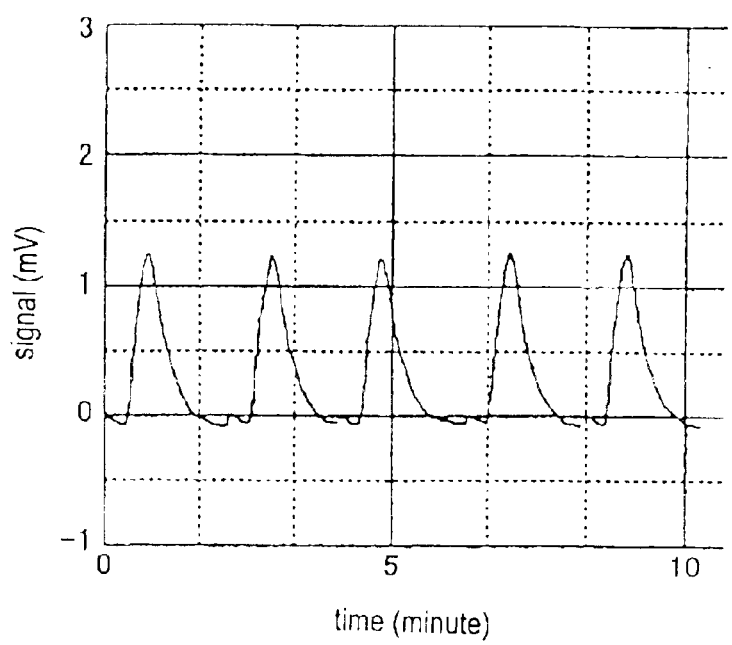
FIG. 4 is a waveform showing signals detected by an infrared gas analyzer of the embodiment.

Extra-pure water to be used on a semiconductor production line and the like as sample water is measured and the results thereof are shown in FIG. 4. FIG. 4 shows outputs of the infrared gas analyzing portion 42, wherein the sample cell and reference cell are alternately detected by the non-dispersion type infrared light meter. Since the measured result does not include the impurity concentration contained in the oxidizing agent, the detected intensity entirely corresponds to the carbon concentration in the sample water.

The same sample water was divided into five portions, which were respectively measured to obtain the results of 2.31, 2.27, 2.52, 2.47 and 2.49 $\mu$/l. An average value of the measured values was 2.41 $\mu$g/l and the standard deviation was 0.11 $\mu$g/l. As a result, it is realized that the measured value on a 2 ppb level can be measured with an excellent repeatability, such as a variation coefficient of 4.73%.

Since the measured value indicates a total concentration of total organic carbon (TOC) and inorganic carbon (IC), in case the TOC concentration is obtained, the IC concentration obtained by using the IC sparger 10 is extracted from the total concentration.

In the embodiment, the present invention is applied to the TOC meter. However, the present invention can be also applied to an apparatus for analyzing a nitrogen compound and a phosphorus compound contained in sample water in a small amount.

In the present invention, when the sample is injected into the oxidation reaction portion, the oxidizing reagent from which the impurities were already removed exists in the oxidizing reaction portion. Therefore, when the sample is measured, the oxidizing reagent does not have any background, or if any, the background is very low. Thus, there is no influence of the concentration of the impurities contained in the oxidizing reagent added to the measured value.

While the invention has been explained with reference to the specific embodiments of the invention, the explanation is illustrative and the invention is limited only by the appended claims.

What is claimed is:

1. An oxidation decomposition element analyzer comprising, a sample supply portion for supplying a sample to be analyzed, an oxidation reagent supply portion for supplying an oxidation reagent, an oxidation reaction portion connected to the sample supply portion and the oxidation reagent supply portion to receive the sample and the oxidizing reagent for reaction, an analyzing portion connected to the oxidation reaction portion for analyzing an oxidized component to be measured to obtain a concentration of the component, and a controlling portion electrically connected to the sample supply portion, oxidation reagent supply portion and oxidation reaction portion, said controlling portion having means for controlling operations of supplying the sample and the oxidation reagent to the oxidation reaction portion such that the oxidation reagent is supplied to the oxidization reaction portion before the sample is supplied thereto and the sample is supplied after elapse of time during which impurities contained in the oxidation reagent are removed through an oxidization decomposition at the oxidization reaction portion.

2. An oxidation decomposition element analyzer according to claim 1, further comprising a carrier gas supply portion for supplying a carrier gas to the oxidation reaction portion, and an inorganic carbon sparger connected to the analyzing portion for measuring inorganic carbon concentration.

3. An oxidation decomposition element analyzer according to claim 2, wherein the oxidation reaction portion includes an ultraviolet lamp so that organic materials contained in the sample injected therein are entirely oxidized by the oxidation reagent and ultraviolet rays to be converted into carbon dioxide.

4. An oxidation decomposition element analyzer according to claim 3, wherein said analyzing portion is an infrared gas analyzer.

* * * * *